United States Patent [19]

Willard

[11] Patent Number: 4,474,886

[45] Date of Patent: Oct. 2, 1984

[54] METHOD FOR EARLY DETECTION OF INFECTIOUS MONONUCLEOSIS BY IDENTIFYING INMONO PROTEINS

[75] Inventor: Karen E. Willard, Woodridge, Ill.

[73] Assignee: The United States of America as represented by the United States Department of Energy, Washington, D.C.

[21] Appl. No.: 406,830

[22] Filed: Aug. 10, 1982

[51] Int. Cl.$^3$ .................... G01N 33/68; G01N 33/50; G01N 27/26
[52] U.S. Cl. .................... 436/63; 204/180 G; 204/403; 260/112 R; 436/56; 436/86; 436/812
[58] Field of Search .............. 204/180 R, 180 G, 1 T, 204/403; 436/812, 86, 63

[56] References Cited

U.S. PATENT DOCUMENTS

| | | | |
|---|---|---|---|
| 4,244,803 | 1/1981 | Aladjem | 204/180 G X |
| 4,301,142 | 11/1981 | Enders | 436/812 X |
| 4,322,274 | 3/1982 | Wilson | 204/180 G |

OTHER PUBLICATIONS

MacKinney, Jr., Archie A., Blood, vol. 32(2), 217–224 (1968).
Willard, Karen E., Clin. Chem., vol. 28(4), 1031–1035 (1982).
Edwards, Jesse J. et al., Clin. Chem., vol. 28(1), 160–163 (1982).

Primary Examiner—Sidney Marantz
Attorney, Agent, or Firm—William Lohff; James W. Weinberger; Michael F. Esposito

[57] ABSTRACT

Early detection of infectious mononucleosis is carried out using a sample of human blood by isolating and identifying the presence of Inmono proteins in the sample from a two-dimensional protein map with the proteins being characterized by having isoelectric banding as measured in urea of about −16 to −17 with respect to certain isoelectric point standards and molecular mass of about 70 to 75 K daltons as measured in the presence of sodium dodecylsulfate containing polyacrylamide gels, the presence of the Inmono proteins being correlated with the existence of infectious mononucleosis.

6 Claims, 17 Drawing Figures

METHOD FOR EARLY DETECTION OF INFECTIOUS MONONUCLEOSIS BY IDENTIFYING INMONO PROTEINS

CONTRACTUAL ORIGIN OF THE INVENTION

The U.S. Government has rights in this invention pursuant to Contract No. W-31-109-ENG-38 between the U.S. Department of Energy and the University of Chicago representing Argonne National Laboratory.

BACKGROUND OF THE INVENTION

This invention relates to the early detection of infectious mononucleosis and more particularly, to a method of early detection based on the analysis of a blood sample to determine the presence of a particular protein or combination of proteins identifiable by isoelectric banding and molecular mass within specific ranges as an indicator of the presence of infectious mononucleosis.

Infectious mononucleosis is an acute self-limited infectious disease of the reticuloendothelial system, primarily involving the lymphatic tissues. The infection is caused by the Epstein-Barr virus and is characterized by the formation of atypical lymphocytes, which have the the appearance of blast cells. These lymphocytes are not specific for infectious mononucleosis and occasionally are confused with lymphoblasts of acute lymphocytic leukemia.

One of the main reasons for clinical interest in the diagnosis of infectious mononucleosis is that it imitates many diseases, some of them more serious, some requiring surgical intervention, and some with serious prognostic implications. In the past, a common detection method has been identified as the MONOSPOT (a trademark of Ortho Diagnostics of Rairton, N.J.) test which utilizes a differential absorption of the patient's serum or plasma to distinguish the specific heterophile antibody against the E-B virus from other heterophile antibodies. However, this method is not always sensitive to the disease at an early stage and does not provide results to distinguish between infectious mononucleosis and certain other diseases such as acute lymphocytic leukemia. If infectious mononucleosis could be detected at an earlier stage, the recovery period for a patient might be significantly reduced. In addition, a detection method which distinguishes between mononucleosis and lymphocytic leukemia could enable physicians to start an effective treatment for the particular disease at an earlier stage.

One object of the invention is a method of detecting mononucleosis at an early stage. A second object is a method of detecting infectious mononucleosis by a relatively simple sampling technique. Another object of the invention is a method for early detection of infectious mononucleosis which has a relatively high degree of reliability. A further object is a method of detecting infectious mononucleosis which may be used for screening patients. Yet another object of the invention is a method of detecting infectious mononucleosis which could also be used for distinquishing it from other abnormalities including lymphocytic leukemia. These and other objects of the invention will become apparent from the following des- cription.

SUMMARY OF THE INVENTION

Briefly, the invention relates to a method of detecting infectious mononucleosis by testing a blood sample of a human to determine the presence or absence of a particular protein (referred to as Inmono:1) in the blood sample, the presence of the protein being correlated with the presence of infectious mononucleosis to a high degree of reliability. In particular, the method involves the isolation and identification of the protein by techniques including the use of two-dimensional electrophoresis to produce a white blood cell protein map. The method may be used to determine if a patient, whose tests indicate the presence of infectious mononucleosis or lymphocytic leukemia, has infectious mononucleosis or by elimination and subsequent morphological analyses, lymphocytic leukemia. In the inventive detection method, the presence of increased amounts of a second protein (referred to as Inmono:2) in combination with Inmono:1 further serves to indicate the presence of infectious mononucleosis.

DETAILED DESCRIPTION OF THE PREFERRED EMBODIMENT

Figure 1A:
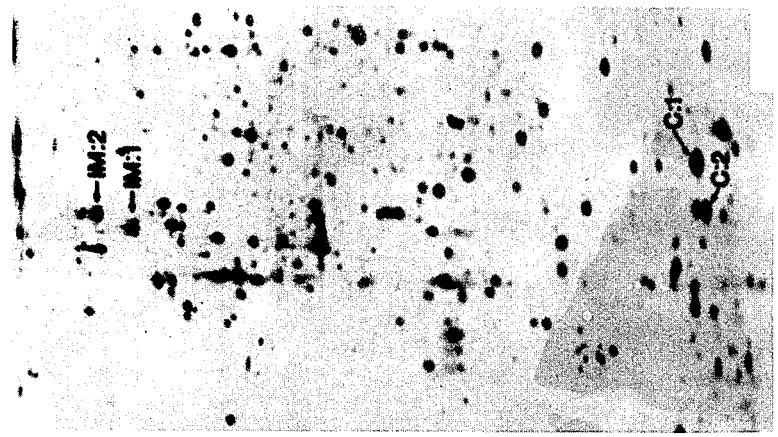
FIG. 1A is a reproduction of a blood protein map from a healthy 25-year-old woman.

Infectious mononucleosis is caused by the Epstein-Barr virus and is considered to be a lymphoproliferative disease, distinguished from lymphoma only by its tendency to spontaneous regression. These lymphocytes are not specific for infectious mononucleosis and occasionally are. confused with lymphoblasts of acute lymphocytic leukemia. In addition to infectious mononucleosis, the Epstein-Barr virus is also associated with at least two other distinct diseases, Burkitt's lymphoma (a lymphoid malignancy) and nasopharyngeal carcinoma (an epithelial malignancy). Although this constitutes a paradox to some extent, there may be genetic factors that determine the outcome of exposure of an individual to Epstein-Barr virus and/or other etiologic agents that may also be involved in the disease. Therefore, a system that could reduce the difficulties of differential diagnosis as well as detecting the disease at an early stage would be of great clinical usefulness.

The inventor has provided a method for detecting the presence of infectious mononucleosis with a high degree of reliability by testing a blood sample from a patient or donor to isolate and detect any Inmono:1 proteins in the sample, the presence of these proteins serving as an indicator of the presence of mononucleosis. These proteins are further characterized by having slightly acidic isoelectric banding as measured in the presence of urea of about $-16$ to $-17$ (with respect to certain isoelectric point standards), and molecular mass of about 70 to 75 K daltons as measured in the presence of sodium dodecylsulfate containing polyacrylamide gels. The isoelectric point standards are described in Anderson, N. L., and Hickman, B. J., *Analytical Techniques for Cell Fractions*, XXIV, Isoelectric Point Standards for Two-Dimensional Electrophoresis, Anal. Biochem. 93, 312–320 (1979), which is hereby incorporated herein by reference.

Advantageously, the blood is treated to separate the white blood cells from the serum, red blood cells and other components in the blood sample in order to more effectively isolate and detect the Inmono:1 proteins. Also, the lymphocytes associated with the white blood cells are advantageously radioactively labeled in order that the Inmono:1 proteins are more readily detected at low levels. Bone marrow samples can also be analyzed by the same procedure.

After separation of the white blood cells and radioactive labeling, the protein components are further separated using two-dimensional electrophoresis to form a two-dimensional protein map with a zone defined by the above described isoelectric banding in the pH range of 5–7 (as measured in urea), or about −20 to −5 based on the isoelectric point standards, and molecular mass in the range of 50 K to 100K daltons. In two-dimensional electrophoresis, the proteins are separated in a first dimension according to isoelectric focusing and in a second dimension according to molecular weight sieving to form the two-dimensional protein map. Measurement of the isoelectric banding is based on internal CK standards developed by the use of carbamylated creatine phosphokinase. If the sample has not been radioactively labeled, the proteins may be stained for analysis by an optical display using conventional analysis techniques. Conventional two-dimensional electrophoresis techniques are described by Anderson et al. in Clinical Chemistry, Vol. 25, No. 7, 1199–1210 (1979), and Analytical Biochemistry, 85, 331–345 (1978).

In general, the technique is carried out by using gel electrophoresis to separate proteins in a first dimension as they move through the gel and focus into clearly delineated bands according to their isoelectric values in urea. A detergent is then added to the gel which binds to the proteins that are then separated electrophoretically in a second dimension according to molecular mass as measured by daltons. When the two-dimensional display or protein map is made visible with a protein stain, the result is a grid-like series of protein spots, the proteins separated in the first dimensions by their electrical charge and in the second dimension by their molecular mass. In general, the isoelectric separations in the map may range from a pH of about 3–10 (or about −25 to beyond zero based on the isoelectric point standards) and it is possible to map proteins as the basis of molecular mass which vary from approximately 10,000 to 200,000 daltons. As further information is obtained regarding various proteins which may appear in the map, a single display map for a patient may possibly be utilized to provide information on more than one disease or change in the biochemistry of other organs of his body.

Figure 1B:
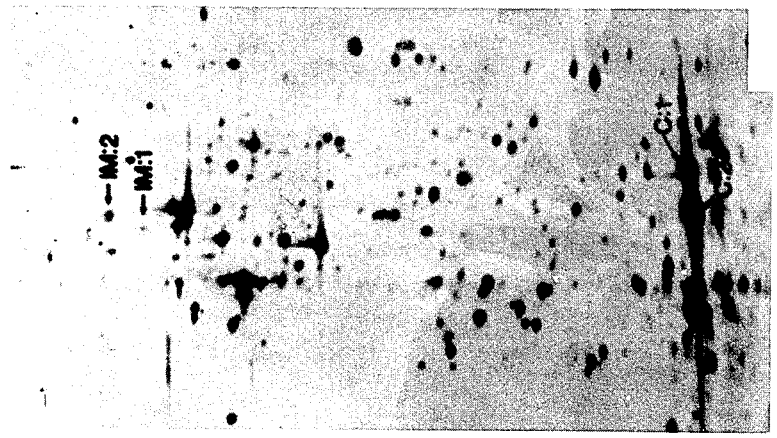
FIG. 1B is a reproduction of a blood protein map from a 20-year-old man with infectious mononucleosis.

The Inmono:1 proteins appear in the map usually as a single spot within the defined range of values. As shown in FIG. 1B, the Inmono:1 proteins may be detected visually.

The inventive method further provides advantages for screening patients for infectious mononucleosis in which blood samples are obtained and tested for the presence of Inmono:1 proteins. Also, the method may be utilized for distinguishing between infectious mononucleosis and lymphocytic leukemia.

Before separation by two-dimensional electrophoresis techniques, the blood sample or samples are advantageously treated to isolate lymphocytes, label lymphocytes radioactively, and harvest radiolabeled lymphocytes. Preferably, the method is carried out as follows:

Isolation of Lymphocytes (1) Blood is collected by venipuncture into heparinized or EDTA treated tubes (Venoject tubes, Kimble-Terumo, Inc., Elkton, Md. 21921).

(2) Fresh blood is rocked for approximately 10 min. after collection on an Ames aliquoit mixer (or the equivalent) until blood has been collected from all donors. Isolation of lymphocytes should begin within 1–2 hours of collection.

(3) Venous blood is centrifuged for 15 min. at $500 \times g$ to obtain buffy coat lymphocytes.

(4) Serum is removed and the lymphocytes are drawn off, diluted in 3 ml of RPMI 1640 medium, and rocked for 5–10 min. to fully oxygenate the blood. This can be visually determined by a change in the color of the sample from dark red to a brighter cherry red. At this stage plain silicone coated Venoject Tubes (10 ml, No. KY-200, Kimble-Terumo), are used.

(5) After rocking the blood samples, 3 ml of Ficoll-/Paque (pharmacia) is underlaid to prepare the gradient.

(6) Gradients are centrifuged for 25 min. at $400 \times g$ to separate the lymphocytes.

(7) The lymphocyte band is harvested, diluted in RPMI 1640, and washed twice in RPMI 1640 at 4° C.

(8) A final wash is done at RPMI minus methionine (made from a GIBCO Selectamine Kit).

(9) Cells are resuspended in RPMI 1640 minus methionine containing 5% FBS, 100 units/ml of Penicillin G, 10 μg/ml Streptomycin, 50 μg/ml Gentamicin, and 0.1% mercaptoethanol (buffered solution, Sigma Chem. Co., No. 365-5) at concentrations up to $1 \times 10^7$ cell/ml.

Labeling of Lymphocytes (1) Cells are cultured in multi-well plates (2.2 ml volume, Falcon) for the labeling experiment.

(2) Each well contains about 400 μl of the cell suspension (thus each well usually contains about $1-4 \times 10^6$ cells) and 25–50 μCi ($^{35}S$) methionine (specific activity 1200 Ci/mM, Amersham).

(3) Cells are incubated at 37° C., 95% r.h., and 5% $CO_2$ on a rocker (Ames aliquoit mixer) for approximately 18 hours.

Harvesting of Lymphocytes (1) Cells are removed from the tissue culture wells with a Pasteur pipette, rinsing the well several times with the cell suspension.

(2) The cell suspension is transferred into a 400 μl microfuge tube (0.4 ml microsedimentation collection tubes, Sarstedt No. 702).

(3) The cells are then centrifuged out of the labeling medium by a 2 sec. spin in the microfuge. The cell pellet will be in the capillary tip of the tube. Only one sample is centrifuged at a time. It is important to work quickly at this stage, and the cell pellets must be solubilized immediately.

(4) The radioactive labeling medium is aspirated into a trap using a needle aspirator and the cell pellets are resuspended in 50 μl of the lysis buffer (of the composition set forth below) using a 100 μl hamilton syringe. Best results are obtained when the cell pellet is resuspended in the buffer, the mixture immediately redrawn into the hamilton syringe, and then placed back into the microfuge tube.

(5) After all the samples have been lysed, the samples may be stored at −80° C. for months without any degradation of the proteins (the half-life of the radiolabel used will ultimately determine the shelf life of the sample).

(6) All samples are centrifuged for 1 min. in a microfuge immediately prior to loading on the first dimension gels. Samples must be recentrifuged after each freeze/thaw cycle. The lysis buffer is composed of
4% NP-40,
9.5 M urea,
2% 2-mercaptoethanol, and
2% ampholines (9–11), with a pH of 9.5.
100 ml of this buffer are frozen at −80° C. in 1 ml aliquoits.

The following examples are provided for illustrative purposes and are not intended to be restrictive as to the scope of the invention:

EXAMPLES I-III

Tests were run on human peripheral blood lymphocytes from normal donors and from patients with infectious mononucleosis. In the first stage associated with isolation of the leukocytes, peripheral blood (or bone marrow) was collected by venipuncture or bone marrow aspiration into EDTA-treated tubes, stored at about 4° C. until pickup from the hospital laboratory (within six hours of collection), and then centrifuged for 15 min. at 500×g to obtain buffy coats. Buffy-coat leukocytes were diluted threefold in RPMI 1640 medium and the lymphocytes (containing monocytes and a small portion of contaminating granulocytes) were isolated by Ficoll-Paque gradient centrifugation. Enriched lymphocyte preparations or "leukocytes" were washed twice in RPMI 1640 medium, and finally washed in RPMI 1640 containing no methionine.

In the labeling of leukocyte proteins, purified leukocytes (enriched for lymphocytes) were cultured in flat-bottomed, multi-well plates at concentrations of up to $4 \times 10^6$ cells per well in a total volume of about 400 μl. Cells were cultured in RPMI 1640 labeling medium (contains no nonradioactive methionine) supplemented with fetal bovine serum (50 ml/l), 2 mercaptoethanol ($4 \times 10^{-5}$ mol/l), and 25–50 μCi of ($^{35}$S) methionine (spec. acty. 1200 kCi/mol). Cultures were incubated at 37° C. in a humidified atmosphere containing five volumes of $CO_2$ per 100 volumes, for 18 hr.

At the end of the labeling period, leukocytes (enriched for lymphocytes) were harvested by centrifugation in a microcentrifuge and the cell pellets were lysed in a pH 9.5 buffer containing per liter, 40 ml of Nonidet P-40 surfactant, 9 mol of urea, 20 ml g ampholytes (9–11), and 50 ml of mercaptoethanol with a pH of 9.5. Solubilized samples were microcentrifuged for 30 sec. to sediment the insoluble material. The soluble proteins were analyzed by high-resolution two-dimensional electrophoresis to resolve the acidic and neutral proteins. The ISO gels used in the first-dimension separation contained pH 3.5–10 Ampholines. Internal isoelectric-point standards, produced by carbamylation of rabbit-muscle creatine kinase were used to standardize the first dimension isoelectric focusing. Second dimension slab gels were formed with a 10–20% linear gradient of polyacrylamide. Molecular weight standards made from rat heart homogenate were used to standardize the molecular weight separation.

Figure 1C:
FIG. 1C is a reproduction of a blood protein map from a 22-year-old infectious mononucleosis patient.
Figures 2A, 2B, 2C, 2D:
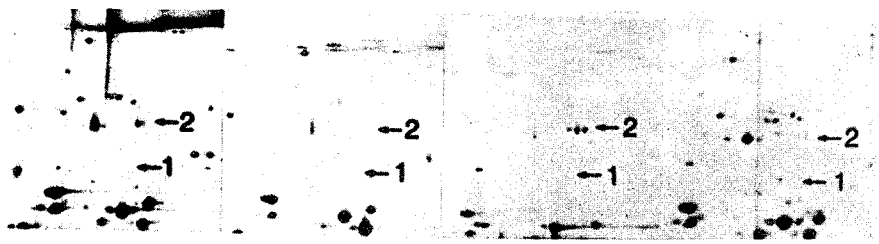
FIGS. 2A–D are four reproductions of portions of blood protein maps for four controls.
Figures 2E, 2F, 2G, 2H:
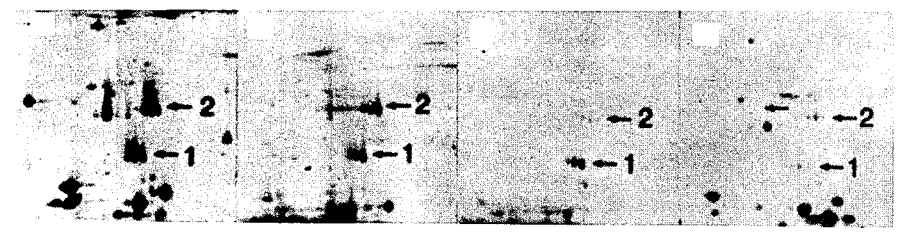
FIGS. 2E–L are eight reproductions of portions of blood protein maps for eight patients with infectious mononucleosis.
Figures 2I, 2J, 2K, 2L:

Two-dimensional gel autoradiographs or blood protein maps of human leukocyte proteins were obtained for each blood sample. FIGS. 1A, 1B, and 1C are representative of the results. FIG. 1A shows a two-dimensional pattern of peripheral blood leukocytes from a healthy 25-year-old woman with a leukocyte count of 5900/mm$^3$ and a differential count showing no detectable amounts of Inmono:1 were detected within the defined ranges. FIG. 1B is a bone marrow leukocyte pattern from a 20-year-old man with infectious mononucleosis whose MONOSPOT test result was negative from the peripheral blood and bone marrow samples taken at the time of the two-dimensional gel analysis. The leukocyte count from his peripheral blood was 4500/mm$^3$, with 30% lymphocytes. As revealed in FIG. 1B, the test was positive as indicated by both the appearance of Inmono:1 and the generally increased level of Inmono:2 in the leukocyte pattern. The Inmono:2 proteins appeared within the isoelectric banding of about −15 to −16 and molecular mass of about 75 to 80K daltons. These proteins were detected in the bone-marrow sample, however, increases could not be detected in the pattern from peripheral blood. Three weeks later, the patient's blood finally gave a positive result in the MONOSPOT test.

FIG. 1C is a pattern of peripheral blood leukocytes from a 22-year-old male IM patient whose MONOSPOT test was strongly positive. At the time of the two-dimensional gel analysis, this patient had a leukocyte count of 20,100/mm$^3$ and the differential count demonstrated 73% lymphocytes, with many atypical lymphocytes. As revealed in FIG. 1C, Inmono:1 was present as was a significant amount of Inmono:2.

EXAMPLES IV-XV

FIG. 2A–L represents sections of blood protein maps with the zone where Inmono:1 and Inmono:2 appear. FIG. 2A–D represents four controls while FIG. 2E–L represents eight patients with positive MONOSPOT tests. As revealed in these maps, Inmono:1 was not detectable in FIG. 2A–D while it was detectable in FIG. 2E–L. Age matched control samples from normal healthy donors were taken and processed simultaneously with the MONO samples. The relative abundance of the Inmono:1 and Inmono:2 proteins can then be compared by eye or computer analysis.

EXAMPLES XVI-XVII

Figure 3B:
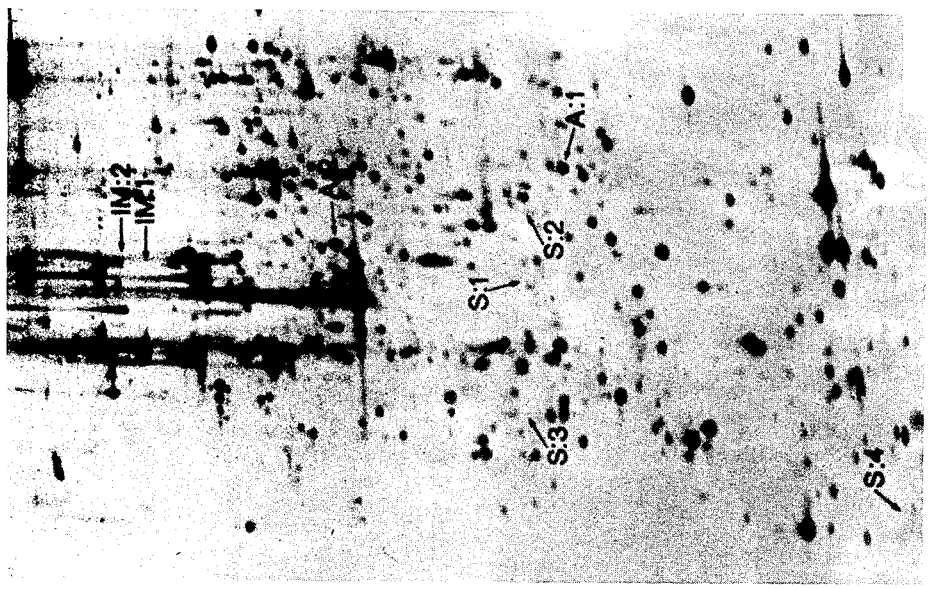
FIG. 3B is a reproduction of a blood protein map for a 16-year-old male with acute lymphocytic leukemic in acute blast crisis.
Figure 3A:
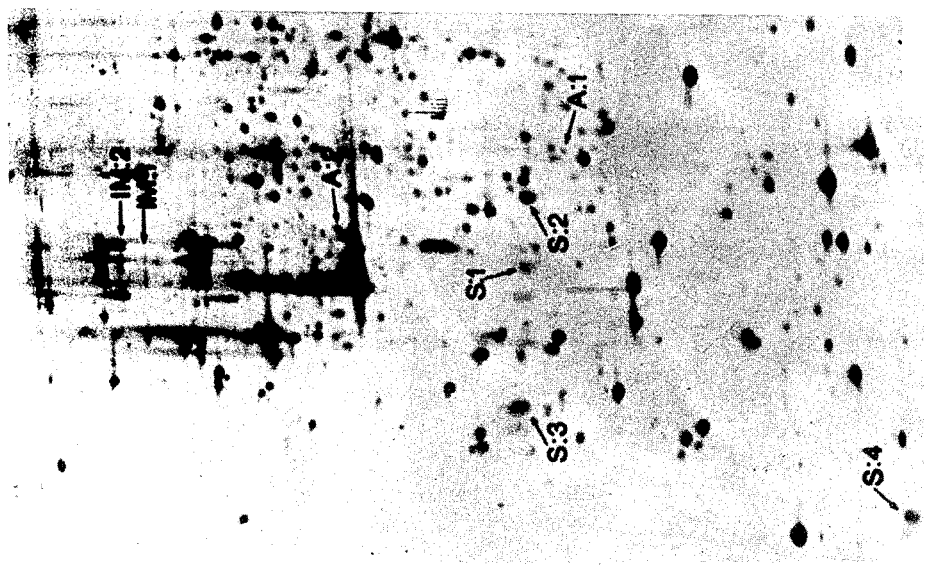
FIG. 3A is a reproduction of a blood protein map for a healthy 20-year-old man.

FIG. 3A–B represents blood protein maps for a healthy 20-year-old man (FIG. 3A) and for a 16-year-old male (FIG. 3B) with acute lymphocytic leukemia in acute blast crisis, at the time of initial diagnosis, before any treatment. Equal amounts of Inmono:2 are detectable in both patterns, but Inmono:1 was not detectable in either sample. Analysis of blood from two other acute lymphocytic leukemia patients during blast crisis also failed to detect any Inmono:1.

Based on further work, Inmono:1 and Inmono:2 proteins have been further characterized as not being viral proteins or induced by the E-B virus in the host cell.

As described above, the invention is useful in detecting infectious mononucleosis by detecting the presence of Inmono:1 proteins in a blood sample, the presence of Inmono:1 proteins being correlated with the presence of infectious mononucleosis to a high degree of reliability. When the patient is normal, the Inmono:1 proteins as indicated in FIG. 1A, are not present in a detectable amount based on the results from two-dimensional analysis of the proteins in the blood sample. By use of the invention, infectious mononucleosis may be detected at an early stage which permits early treatment.

The embodiments of the invention in which an exclusive property or privilege is claimed are defined as follows:

1. A method for the detection of infectious mononucleosis in a human subject comprising:
   (a) collecting a sample of blood from said human subject, and
   (b) determining the presence of said mononucleosis with a high degree of reliability including the steps of isolating and identifying any Inmono:1 proteins in the sample, said Inmono:1 proteins being characterized by:
      (i) having acidic isoelectric banding as measured in the presence of urea of about −16 to −17 with use of CK charge standards, and
      (ii) having molecular mass of about 70 to 75K daltons as measured in the presence of sodium dodecylsulfate containing polyacrylamide gels, and
   (c) correlating a positive result from step (b) with the presence of infectious mononucleosis in the human subject.

2. The method of claim 1 where said isolating and identifying steps include:
   (a) isolating lymphocytes in the sample,
   (b) separating proteins in said lymphocytes in a first dimension, according to isoelectric equilibrium and in a second dimension according to molecular mass to form a two-dimensional protein map with a zone defined by isoelectric banding as measured in urea of about −20 to −5 with the use of CK charge standards and molecular mass within the range of 50 to 100K daltons, in sodium dodecylsulfate, and
   (c) determining the presence of any of said Inmono proteins in said zone, the presence of said Inmono proteins being correlated with the presence of said mononucleosis.

3. The method of claim 2 including the step of determining the presence of a second Inmono protein in said zone, the second Inmono protein being defined by said isoelectric banding of about −15 to −16 with the use of CK charge standards and molecular mass within the range of 75 to 80K daltons.

4. The method of claim 2 wherein said isolating and identifying steps include the step of radioactively labeling said lymphocytes for ease in detection.

5. The method of claim 2 wherein said Inmono proteins are stained for an optical display.

6. A method of screening human patients for the early detection of infectious mononucleosis comprising:
   (a) collecting blood samples from the patients,
   (b) determining the presence of said mononucleosis with a high degree of probability for each patient including the steps of testing each sample for the presence of any Inmono:1 proteins as an indicator, said Inmono:1 proteins being characterized by:
      (i) having acidic isoelectric banding as measured in the present of urea of about −16 to −17 on CK standards, and
      (ii) having molecular mass of about 70 to 75K daltons as measured in the presence of sodium dodecylsulfate containing polyacrylamide gels, and
   (c) correlating a positive result from step (b) with the presence of infectious mononucleosis in the human subject.

* * * * *